United States Patent
Larson

(12) 
(10) Patent No.: US 6,562,864 B1
(45) Date of Patent: May 13, 2003

(54) CATECHIN MULTIMERS AS THERAPEUTIC DRUG DELIVERY AGENTS

(76) Inventor: Drake Larson, P.O. Box 355, Thermal, CA (US) 92274

( * ) Notice: Subject to any disclaimer, the term of this patent is extended or adjusted under 35 U.S.C. 154(b) by 0 days.

(21) Appl. No.: 10/137,368

(22) Filed: May 3, 2002

Related U.S. Application Data

(63) Continuation-in-part of application No. 09/655,400, filed on Sep. 5, 2000, now Pat. No. 6,423,742.
(60) Provisional application No. 60/329,247, filed on Oct. 12, 2001, and provisional application No. 60/152,172, filed on Sep. 2, 1999.

(51) Int. Cl.[7] .................... A61K 31/35; A61K 31/19
(52) U.S. Cl. .................. 514/453; 514/456; 514/824; 549/354; 549/355
(58) Field of Search ................. 514/453, 456, 514/824; 549/354, 355

(56) References Cited

U.S. PATENT DOCUMENTS

| | | | |
|---|---|---|---|
| 3,882,248 A | | 5/1975 | Igimi et al. |
| 4,226,788 A | | 10/1980 | DeLuca et al. |
| 4,707,360 A | | 11/1987 | Brasey |
| 5,470,877 A | | 11/1995 | Gould et al. |
| 5,648,377 A | | 7/1997 | Bombardelli et al. |
| 5,855,944 A | | 1/1999 | Koschinski et al. |
| 6,054,128 A | * | 4/2000 | Wakat ............. 424/195.1 |
| 6,133,311 A | | 10/2000 | Bok et al. |
| 6,214,868 B1 | * | 4/2001 | Ahn et al. ........... 514/456 |
| 6,420,572 B1 | * | 7/2002 | Romanczyk, Jr. et al. .. 549/400 |
| 6,423,742 B1 | | 7/2002 | Larson |
| 2002/0018807 A1 | * | 2/2002 | Schmitz et al. ......... 424/450 |

FOREIGN PATENT DOCUMENTS

| | | |
|---|---|---|
| DE | 1991 5102 | 10/2000 |
| JP | 07 223 941 | 9/1995 |

OTHER PUBLICATIONS

Sears, "Sulfonation of Catechin". J.Org.Chem., vol. 37,No.22, 3546–47, 1972.*

(List continued on next page.)

Primary Examiner—Samuel Barts
Assistant Examiner—Devesh Khare
(74) Attorney, Agent, or Firm—Chalin A. Smith; Smith Patent Consulting

(57) ABSTRACT

Described herein are catechin multimers, and particularly substituted catechin multimers, and their use as carrier moieties for the delivery of nucleophilic and cationic bioactive therapeutic agents to target sites in vivo. For example, substituted catechin multimers of the present invention may be administered alone, for the treatment of stenotic vascular diseases and disorders, such as atherosclerosis (also known as arteriosclerosis) and coronary heart disease (also known as coronary artery disease and ischemic heart disease). Alternatively, catechin multimers, substituted and otherwise, may be complexed with nucleophilic and/or cationic bioactive therapeutic agents, such as anti-thrombotic agents, cholesterol lowering agents, anti-plaque agents, anti-cancer agents, chemotherapeutic agents, anti-inflammatory agents, antibiotics, antimicrobials, wound healing agents, and the like, for the treatment of a variety of diseases and disorders, including but not limited to cardiac and vascular stenoses, cancer, inflammatory conditions, neurological conditions, infection, wounds, burns and the like. The catechin multimers, particularly the substituted catechin multimers, described herein have a strong affinity for polar proteins residing in the vascular endothelium as well as cell walls and membranes, and, accordingly, are able to provide targeted delivery of bioactive agents embedded therein and/or complexed therewith so as to potentiate their therapeutic effects. The therapeutic complexes may be pharmaceutically formulated "neat" (e.g., without additives) or with additives such as pharmaceutical carriers, diluents, buffers, adjuvants, excipients, surfactants, and stabilizers.

21 Claims, 1 Drawing Sheet

OTHER PUBLICATIONS

Silverman, "The organic chemistry of drug design and drug action". Academic Press,Inc., pp. 15–22, 1992).*
*Tarasova, Fenol'nye Soedin. Ikh Biol. Funkts., Mater. Vses. Simp., 1 Sup: 377–83 (1968)—Abstract only.
*Crowell et al., Cancer Chemother. Pharmacol., vol.. 35(1):35–7 (1994)—Abstract only.
*De Feyter et al., Eur. Heart J., 16 Suppl. I: 26–30 (1995)—Abstract only.
*Fulton et al., J. Surg. Res., vol. 69 (1): 128–34 (1997)—Abstract only.
*Ikechukwu et al., J. Chromatogr. B. Biomed Sci. Appl., vol. 688(2):354–8 (1997)—Abstract only.
*Phillips et al., Drug Metab. Dispos., vol. 23 (7):676–80 (1995)—Abstract only.
*Schaefer et al., J. Investig. Med., vol. 45 (9): 536–41 (1997)—Abstract only.
*Thompson, GR, Cardiology, vol. 77 Suppl. 4: 65–69 (1990)—Abstract only.
*Uedo et al., Cancer Letters, vol. 137:131–136 (1999)—Abstract only.
*Vigushi et al., Cancer Chemother. Pharmacol., vol. 42(2): 111–7 (1998) Abstract only.
*Yamakoshi et al., Atherosclerosis, vol. 142(1):139–49 (1999)—Abstract only.
*Zhang et al., J. Gas Chromatogr. B. Biomed Sci. Appl., vol. 728(1):85–95 (1999)—Abstract only.
KA Steinmetz, JD Potter. Vegetables, fruit and cander. I. Epidemiology. Cancer Causes Control 2: 325–357, 1991—Abstract only.
MG Hertog, EJ Feskens, PC Hollman, MB Katan, D Kromhout. Dietary antioxidant flavonoids and risk of coronary heart disease: the Zutphen Elderly Study. Lancet 342: 1007–1011, 1993.—Abstract only.
SE Norell, A Ahlbom, R Erwald, G Jacobson, I Lindberg–Navier, R Olin, B Törnberg, K–L Wiechel, Diet and Pancreatic cancer: a case–control study. Am J Epidemiol 124: 894–902, 1986—Abstract only.
GJ Soleas, EP Diamandis, DM Goldberg. Wine as a biological fluid: history, production, and role in disease prevention. J Clin Lab Anal 11: 287–313, 1997.—Abstract only.
L Bravo. Polyphenols: chemistry, dietary sources, metabolism, and nutritional significance. Nutr Rev 56: 317–333, 1998.—Abstract only.
S Renauld, M de Lorgeril. Wine, alcohol, platelets, and the French paradox for coronary heart disease. The Lancet 339: 1523–1526, 1992.—Abstract only.
M Gronbaek, et al. Mortality associated with moderate intake of wine, beer or spirits. BMJ 310: 1165–1169, 1995—Abstract only.
JP Jost, C Simon, M Nuttens, et al. Comparison of dietary patterns between population samples in the three French MONICA nutritional surveys. Rev Epidemiol Sante Publique 38: 517–523, 1990—Abstract only.
LA Friedman, AW Kimball. Coronary heart disease mortality and alcohol consumption in Framingham. Am J Epidemiol 24: 481–489, 1986.—Abstract only.
RD Moore, TA Pearson. Moderate alcohol consumption and coronary artery disease. A review. Medicine 65: 242–267, 1986.—Abstract only.
RD Langer, MH Criqui, DM Reed. Lipoproteins and blood pressure as biological pathways for effect of moderate alcohol consumption on coronary heart disease. Circulation 85: 910–915, 1992.—Abstract only.
LL Rudel, CW Leathers, MG Bond, MB Bullock. Dietary ethanol–induced modification in hyperlipoproteinemia and atherosclerosis in nonhuman primate (*Macaca nemestrina*). Atherosclerosis 1: 144–145, 1981.—Abstract only.
S Renaud, AD Beswick, AM Fehily, DS Sharp, PC Elwood. Alcohol and platelet aggregation: the Caerphilly prospective heart disease study. Am J Clin Nutr 55: 1012–1017, 1992,.—Abstract only.
J Folts, et al. Administration of wine and grape juice inhibits in vivo platelet activity and thrombosis in stenosed canine coronary arteries. Circulation 91: 1182–1188, 1995.
D Klurfield, D Kritchevsky. Differential effects of alcoholic beverages on experimental atherosclereosis in rabbits. Experimental and Molecular Pathology 34: 62–71, 1981.
J. Yamakoshi, et al. Proanthocyanidin, rich extract from grape seeds attenuates the development of aortic atherosclerosis in cholesterol–fed rabbits. Atherosclerosis 142: 139–149, 1999.
A Bertelli. Modulatory effect of resveratrol, a natural phytoalexin, on endothelial adhesion molecules and intracellular signal transduction. Pharmaceutical Biology 36 supp.: 44–52, 1998.—Abstract only.
D Fitzpatrick, et al. Endothelium–dependent vasorelaxaton caused by various plant extracts. J Cardiovascular Pharmacology 26: 90–95, 1995.—Abstract only.
CR Pace–Asciak, S Hahn, EP Diamandis, G Soleas, DM Goldberg. The red wine phenolics trans–resveratrol and quercetin block human platelet aggregation and eicosanoid synthesis: Implications for protection against coronary heart disease. Clinica Chimica Acta 235: 207–219, 1995.—Abstract only.
WS Kang, IH Lim, DY Yuk, KH Chung, JB Park, HS Yoo, YP Yun. Antithrombotic activities of green tea catechins and (–)–epigallocatechin gallate. Thrombosis Research 96: 229–337, 1999.—Abstract only.
MF Harmand, P. Blanquet. The fate of total flanolic oligomers extracted from vitis vinifera in the rat. Drug Metab Pharmacokin 1:15–30, 1978—Abstract only.
DF Fitzpatrick, R. O'Malley et al. Isolation and characterization of endothelium–dependent vasorelaxing compounds from grape seeds. J. Agriculture Food Chemistry 2000: 48: 6384–6390.
DF Fitzpatrick, et al. Endothelium depend vasorelaxing activity of wine and other grape products. Am. J. Physiol. 265 H774–778, 1993.
S Yao et al Endogenous nitric oxide protects platelet aggregation and cyclic flow variations in stenosed and endothelium injured arteries. Circulation 86: 1302–1309, 1992.
HS Denrow et al., Administration of Wine and Grape Juice Inhibits In Vivo Platelet Activity and Thrombosis in Stenosed Canine Coronary Arteries, American Heart Association (1995)—Abstract only.
MG Hertog et al., Flavonoid Intake and Long Term Risk of Coronary Heart Disease and Cancer in the Seven Countries Study, Arch Intern Med. 155(11):1184 (1995)—Abstract only.
E Revilla et al., Analysis of Several Phenolic Compounds with High Antioxidant Properties in Grape Extracts and Wines by HPLC–Photodiode Array Detection Without Sample Preparation, J. Chromatograph. A., 881:461–469 (2000)—Abstract only.

* cited by examiner

CATECHIN MULTIMERS AS THERAPEUTIC DRUG DELIVERY AGENTS

CROSS-REFERENCE TO RELATED APPLICATIONS

This application is a continuation-in-part of U.S. patent application Ser. No. 09/655,400, filed Sep. 5, 2000 now U.S. Pat. No. 6,423,742, which, in turn, claims the benefit of U.S. Provisional Application Ser. No. 60/152,172, filed Sep. 2, 1999. This application also claims the benefit of U.S. Provisional Application Ser. No. 60/329,247, filed Oct. 12, 2001. The contents of these enumerated applications are incorporated by reference herein in their entirety.

TECHNICAL FIELD AND INDUSTRIAL APPLICABILITY OF THE INVENTION

The present invention is related to catechin multimers and their use as carrier moieties for the delivery of nucleophilic and/or cationic bioactive therapeutic agents to target sites in vivo. For example, substituted catechin multimers of the present invention may be administered alone, for the treatment of stenotic vascular diseases and disorders, such as atherosclerosis (also known as arteriosclerosis) and coronary heart disease (also known as coronary artery disease and ischemic heart disease). Alternatively, catechin multimers, substituted and otherwise, may be complexed with nucleophilic and/or cationic bioactive therapeutic agents, such as anti-thrombotic agents, cholesterol lowering agents, anti-plaque agents, anti-cancer agents, chemotherapeutic agents, anti-inflammatory agents, antibiotics, antimicrobials, wound healing agents, and the like, for the treatment of a variety of diseases and disorders, including but not limited to, vascular and cardiac stenoses, cancer, inflammatory conditions, neurological conditions, infections, burns, wounds, etc. Catechin multimers, particularly the substituted catechin multimers described herein, have a strong affinity for polar proteins residing in the vascular endothelium as well as the walls and membranes of other select cells and tissues, and, accordingly, are able to provide targeted delivery of bioactive agents embedded therein and/or complexed therewith so as to potentiate their therapeutic effects.

BACKGROUND OF THE INVENTION

Many diseases or disorders are characterized by localized pathology, i.e., affecting only select cells, tissues or organs. Examples of such diseases or disorders include but are not limited to cancers, stenotic vascular disorders such as atherosclerosis (or arteriosclerosis), inflammatory disorders, infections, wounds, burns, and certain neurological conditions. Treatment modalities for such diseases often rely on the ability to target bioactive agents to a diseased region or tissue in the body of a patient, while minimizing or preventing action of the bioactive agents on other regions or tissues in the body, such as undiseased regions or tissues. In other words, in treating such conditions, it is desirable to direct the appropriate drug to the affected area while at the same time avoiding unacceptable or toxic side effects to healthy tissue. Targeted drug delivery means are particularly important where the toxicity of the drug is an issue. Specific tissue targeting drug delivery methods potentially serve to minimize toxic side effects, lower the required dosage amounts, and decrease costs for the patient.

Various methods for targeted delivery of bioactive agents are described in the literature. For example, one method involves the use of liposomes as delivery vehicles. Alternatively, structural features, such as receptor proteins and cell-specific antigens, have also been used in targeting delivery of a bioactive agent to a particular region or tissue. However, such structural features are associated with one or, at most a few, disease states. In addition, incomplete or irregular expression of such structural features may further limit their usefulness in targeted delivery of bioactive agents. Moreover, delivery of effective doses of bioactive agents to target cells is hampered by many factors, including but not limited to, low residence times in serum, ineffective targeting, loss of the therapeutic agent in solution before it may be taken up by the target cell, and degradation of the therapeutic in the endosomic/lysosomic pathway.

Accordingly, there is a need in the art to provide new and/or improved methods for targeting specific cells or tissues in the body of a patient, and delivering bioactive agents to such targeted cells or tissues. The present invention is directed to these, as well as other, important ends.

SUMMARY OF THE INVENTION

As demonstrated herein, catechins, including epi and other carbo-cationic isomers and derivatives thereof, can as monomers, dimers and higher multimers can form complexes with nucleophilic and cationic bioactive agents. Catechin multimers have a strong affinity for polar proteins, such as those residing in the vascular endothelium, and on cell/organelle membranes. Thus, as discussed in detail herein, such catechin compounds find particular utility in the targeted delivery of bioactive agents to select sites in vivo.

Accordingly, it is an object of the invention is to provide therapeutic compositions and methods of using same to treat stenotic vascular diseases and disorders, such as atherosclerosis and coronary artery disease, comprising an effective amount of a substituted catechin multimer. In a preferred embodiment, the substituted catechin multimer is an amidated catechin multimer, a complex formed from the reaction between catechin and nitrogen containing moieties such as ammonia ($NH_3$).

Nitric oxide (NO) and cyclic guanosine 3',5'-monophosphate (cGMP) have been reported to prevent vascular smooth muscle cell proliferation and have beneficial effects to reduce intimal thickening in response to arterial injury (See Boerth N J et al., *J Vasc Res July–August* 1997;34(4):245–59). Furthermore, endothelial dysfunction associated with atherosclerosis has been attributed to alterations in the L-arginine-nitric oxide (NO)-cGMP pathway or to an excess of endothelin-1 (ET-1) (See Hernandez-Perera O et al., *J Clin Invest Jun.* 15, 1998;101(12):2711–9). Accordingly, endothelial NO-cGMP signaling appears to be involved in the attenuation of atherosclerosis and inhibition of platelet aggregation. Though not wishing to be bound by theory, it is believed that these substituted catechin multimers, through their affinity for polar proteins of the vascular lining, direct delivery of the nitrogen moieties embedded therein to the vascular endothelium. The nitrogen moieties then stimulate NO-cGMP signaling, which, in turn, attenuates atherosclerosis and platelet aggregation. Thus, in the above context, "treatment" involves one or more of the following: (a) the reduction of plaque formation of the vascular walls; (b) the reversal of plaque deposition and degenerative changes in the arterial walls; and (c) the removal or stabilization of existing vascular plaques; or (d) the enhancement of cholesterol solubility in plasma.

In one embodiment, the substituted catechin multimers, alone or in combination with other bioactive agents, are particularly effective in encouraging or increasing cholesterol solubility and also in reversing the arterial plaque deposition and degenerative changes to substantially arrest, alleviate and, to a certain extent, even cure the many and varied problems, conditions and secondary complications associated with atherosclerosis.

In another embodiment, the substituted catechin multimers and methods of using same provide for the inhibition of the formation (e.g., progression) of atherosclerotic plaques and/or the removal of existing plaque from vascular walls of animals, particularly humans. The therapeutic compositions and methods may further aid in stabilizing plaques. By "plaque stabilization", it is meant the inhibition of plaque passing through a phase in which the lipid core has grown and the fibrous cap is very thin and vulnerable to rupture due to an increase in the density of macrophages.

It is another object of the present invention to provide therapeutic compositions and methods of using same for the targeted delivery of bioactive agents to select sites in vivo, comprising an effective amount of a catechin multimer, particularly a substituted catechin multimer, complexed with a nucleophilic and cationic bioactive agent. In order to facilitate formation of the complex, the bioactive agent should be either naturally nucleophilic and/or cationic or modified to be so. The catechin multimer acts as a "carrier" for the bioactive agent, targeting the tissue of interest, such as the vascular endothelium or the mitochondrial membrane and delivering the therapeutic agent embedded therein to the targeted site. The bioactive agent is preferably selected from the group consisting of anti-thrombotics, cholesterol lowering agents, anti-plaque agents, anti-cancer agents, chemotherapeutics, anti-inflammatory agents, antibiotics, antimicrobials, wound healing agents, and the like.

It is further object of the present invention to provide a method for treating diseases or disorders associated with localized pathology. Examples of such diseases and disorders include but are not limited to cardiac and vascular stenoses, cancer, inflammatory conditions, neurological conditions, infection, wounds, burns and the like.

In one embodiment, the therapeutic composition comprises a catechin multimer, particularly a substituted catechin multimer, complexed with a bioactive anti-cancer or chemotherapeutic agent. The catechin multimer facilitates the targeted delivery of the bioactive agent to the inner mitochondrial membrane of the cancer cell and can stimulate the release of mitochondrial cytochrome c necessary for proper apoptosis.

In another embodiment, the therapeutic composition comprises a catechin multimer, particularly a substituted catechin-ligand multimer, complexed with a bioactive anti-inflammatory agent. The catechin multimer facilitates the targeted delivery of the bioactive agent to an inflamed site and inhibits adhesion of platelets and macrophages. Examples of inflammatory conditions that may be amenable to treatment with such therapeutic compositions include but are not limited to autoimmune disorders (e.g., rheumatoid arthritis and systemic lupus erythematosus), myocarditis, nephritis, ulcerative colitis, inflammatory bowel disease (e.g., Crohn's disease).

In another embodiment, the therapeutic composition comprises a catechin multimer, particularly a substituted catechin multimer, complexed with a bioactive antibiotic or antimicrobial agent, such as zinc or bismuth. The catechin multimer facilitates the targeted delivery of the bioactive agent to an infected site.

The therapeutic compositions of the present invention may be pharmaceutically formulated "neat" or with one or more excipient or additives. For example, therapeutic compositions may comprise one or more stabilizing agents, such as salts, tannic acid, ascorbic acid lecithin, and tocopherols. In one preferred embodiment, the stabilizing agent comprises about 10 wt. % to about 60 wt. % of the entire composition.

These and other objects and features of the invention will become more fully apparent when the following detailed description is read in conjunction with the accompanying figures and examples.

DETAILED DESCRIPTION AND PREFERRED EMBODIMENTS OF THE INVENTION

Figure 1A:
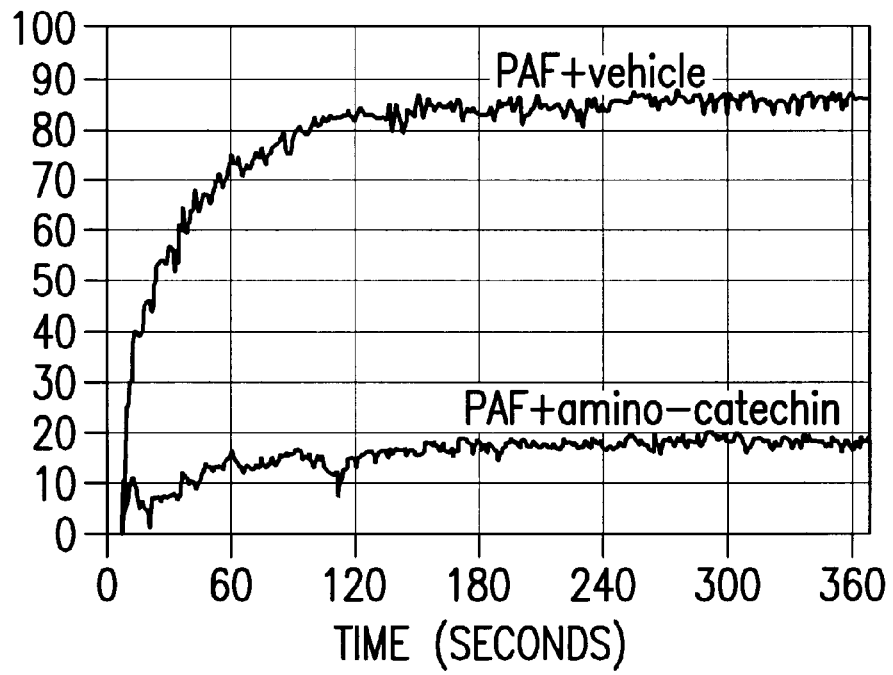
FIG. 1A depicts the results of human platelet aggregation trials using platelet activating factor (PAF) as the aggregating agent, comparing the effect of amidated catechin multimer to control. Time is shown on the X-axis and the percentage of platelets in aggregated state is shown on the Y-axis.

In one embodiment, the present invention relates to therapeutic compositions and methods for treating stenotic cardiac and vascular diseases and disorders, particularly atherosclerosis. Plaque formation on vascular walls of animals, particularly humans, can be reduced by administering to a subject in need thereof a therapeutically effective amount of a catechin multimer, particularly a substituted catechin multimer, or a derivative of such a catechin multimer. Antioxidant stabilizing agents may also be added to induce ligand bonds among the catechin monomers that make up the multimeric unit units. Administration is expected to decrease the formation of plaque on the vascular walls, such as occurs during atherosclerosis. Adhesion of plaque to the vascular walls results from activity of various compounds both aqueous and lipid soluble, cells, and bacteria in the blood. The formulation of the invention minimizes or prevents unhealthy plaque deposits from accumulating on the vascular walls.

In an alternate embodiment, the present invention relates to therapeutic compositions and the use thereof to provide targeted delivery of suitable bioactive agents to select sites in vivo, particularly for the treatment of diseases and disorders associated with localize pathology, such as cancer, inflammation and infection. Suitable bioactive agents include but are not limited to anti-thrombotics, cholesterol lowering agents, anti-plaque agents, anti-cancer agents, chemotherapeutics, anti-inflammatory agents, antibiotics, antimicrobials, wound healing agents, and the like.

At varying concentrations, the therapeutic compositions of the present invention may be formulated as a pill, capsule, powder, liquid, lotion, suppository, spray, dietary supplement or the like, so as to reduce adhesion of plaque to the vascular walls. The particular formulation will determine the mode of administration and vice versa. Exemplary methods of administering the therapeutic formulations include, but are not limited to, oral ingestion, parenteral introduction, topical application, and vaginal, rectal, and nasal delivery. In addition, the therapeutic compositions can be conveniently formulated in lotions and foodstuffs.

A. Substituted Catechin Multimers

Catechin is a bioflavonoid that is found in green tea. It has been demonstrated to have both antiviral and antioxidant qualities. Not only does it appear to prevent oxidative damage to the heart, kidney, lungs, and spleen, but preliminary studies of animals show that catechin prevents oxidative damage to blood as well. See Chen, H. et al., *Free Radic Res* (February 1995) 22(2):177–86 and Chen, H. et al., *Free Radic Biol Med* (May 1995) 18(5):949–53. The molecular formula of catechin and a dimer thereof are shown below:

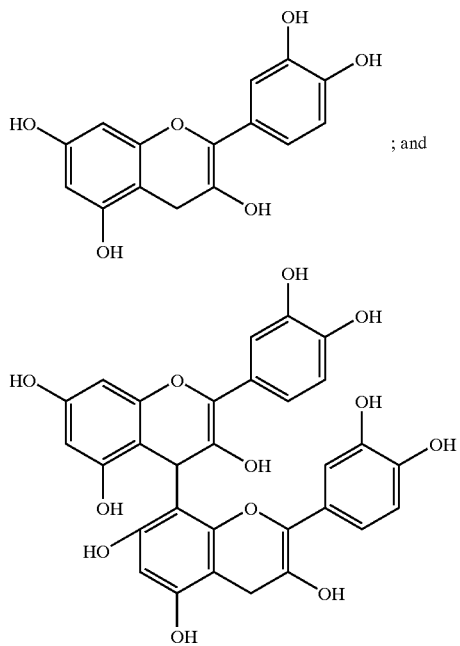

As noted above, the present invention utilizes a multimeric form of catechin or a derivative of such multimer. As used herein, the term "multimer" refers to multivalent or multimeric forms of the compounds of interest. A "multimer" may be made by linking multiple copies (two or more) of a compound (or a derivative thereof) to each other. The multimer may include linking units disposed between the compound copies. Suitable linking units are known in the art and can be routinely selected to arrive at the optimum multivalency and spacing. Useful linking moieties include those containing a multiplicity of functional groups that can be reacted with functional groups associated with the parent compound or its derivative. Such functional groups include, but are not limited to, halo (e.g., fluoro, chloro, iodo, etc.), amino, amido, nitro, sulfhydryl, hydroxyl, and alkylamino groups. These groups are routinely selected to obtain stable linkages between or among the multiple compound copies.

In the context of the present invention, the bonds linking the multiple copies of catechin together into a multimeric form can be transient in nature. In other words, it is conceivable that the catechin multimer may dissociate into monomeric units under certain conditions yet retain its multimeric character under other conditions.

In the context of the present invention, the term "multimer" should be construed to include "polymers", i.e. large molecules formed by the union of at least five identical monomers, usually containing many more than five monomers, and some may contain hundreds or thousands of monomers in each chain.

The catechin multimer may be a "substituted catechin multimer", defined herein as a catechin optionally substituted by one or more nucleophilic functional groups or substituents. Examples of suitable nucleophilic substituents include but are not limited to halo (e.g., F, I, Cl, etc.), guano, amino, amido, nitro, cyano, carbonyl, carboxy, sulfo, sulfoxy, and aceto groups. The nucleophilic substituent moities are interspersed throughout the multimer, typically extending from the hydrocarbon linking units that connect the catechin monomers to each other.

In one embodiment, the substituted catechin multimer is an "amidated catechin multimer". Amidated catechin multimers, also referred to as an amino-substituted catechin multimers, arise from the reaction between catechin and ammonia, an example scheme of which is shown below:

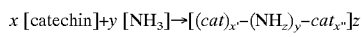

wherein x, x', x", y, and z are integers including zero. The NH moities are interspersed throughout the multimer, typically extending from the hydrocarbon linking units that connect the catechin monomers to each other.

As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with factors as the particular condition being treated, the physical condition of the patient, the type of animal being treated, the duration of the treatment, the nature of concurrent therapy (if any), and the specific formulations employed and the structure of the compounds or its derivatives.

In the case of treating stenotic vascular disorders, an amount would be deemed therapeutically effective if it resulted in one or more of the following: (a) the reduction of plaque formation of the vascular walls; (b) the reversal of plaque deposition and degenerative changes in the arterial walls; (c) the removal or stabilization of existing vascular plaques; or (d) the enhancement of cholesterol solubility in plasma.

In the case of treating other diseases and disorders, such as cancer, inflammatory conditions, neurological conditions, infection, wounds, burns and the like, an amount would be deemed therapeutically effective if it resulted in reduction, inhibition or elimination of at least one pathological symptom associated with the disease. Optimum effective amounts can be readily determined by one of ordinary skill in the art using routine experimentation.

As noted above, the present invention encompasses not only catechin multimers but derivatives of such multimers. As used herein, "derivatives" includes, but are not limited to, oxidation products, salts, solvates, prodrugs, and metabolites of the parent compound of interest (e.g., catechin multimers). Preferred derivatives are those which retain the desirable therapeutic activity of the parent compound. Of particular utility are those derivatives that maintain the beneficial characteristics of the parent compound, have a pleasant flavor, are at least mildly polar, and have a specific gravity close to 1.0 so they can be easily used as fortifiers in liquid beverages.

Exemplary derivatives of catechin include, but are not limited to, quercetin, dihydroquercetin, dihydroquercetin-3-acetate, gallocatechin, geraldol, malvidin, rutin and the like. In the context of the present invention, a catechin multimer may be comprised of monomers units selected from catechin, catechin derivatives, and combinations thereof.

As used herein, "oxidation products" are those compounds resulting from an oxidation reaction. They may be partially or fully oxidized. The term "oxidation" is generally defined as the loss of electrons. Oxidation includes, but is not limited to, those reactions where either a hydrogen is removed or an electronegative element, such as oxygen, nitrogen, or halogen, is added. Any reaction that converts a functional group from a lower oxidation state to a higher one is considered "oxidation". This includes a pathway of polymerizing compounds where the result is the neutralization of oxygen's free radicals via a new compound plus water.

An exemplary oxidation reaction is as follows:

$$R+X+\tfrac{1}{2}(O_2) \rightarrow (R'-X')+H_2O$$

where R, R', X, X' represent compounds and chemical composition of R=R'+H and X=X'+H. R'—R and R'—X' are considered partially oxidized products, multimers of R and/or X.

The catechin multimers, alone and complexed with bioactive agents, may take the form of a salt, prodrug or metabolite. The term "salts" include, but are not limited to, pharmaceutically acceptable addition salts. The functional groups on the active compounds of the present invention can react with any of a number of inorganic or organic bases, or inorganic and organic acids, to form pharmaceutically acceptable addition salts. The salt form of a parent compound is often preferred because it tends to be more soluble in aqueous or other protonic solvents than are the corresponding free-base forms. Exemplary addition salts include, but are not limited to, chlorides, bromides, iodides, acetates, sulfates, sulfites, phosphates, oxalates, malonates, succinates, fumarates, maleates, benzoates, phthalates, sulfonates, propionates, butyrates, citrates, palmitic, lactates, glycollates, and tartrates.

As used herein, the term "solvates" refers to derivative forms a parent compound comprised of the parent structures in combination with solvents. Exemplary solvents include, but are not limited to, water, isopropanol, ethanol, methanol, DMSO, ethyl acetate, acetic acid, or ethanolamine.

As used herein, the term "prodrug" refers to a precursor of a parent compound that is converted within the body into the parent compound itself or an active derivative form thereof having the prescribed therapeutic activity associated with the compound. Prodrugs are particularly useful when the parent compound is too toxic to administer systemically, is absorbed poorly by the digestive tract, or is broken down by endogenous enzymes before it reaches its target.

As used herein, the term "metabolite" of a parent compound refers to any product produced by the body's metabolism of the parent compound. Both prodrugs and metabolites may be identified using routine techniques known in the art.

Some of the compounds described herein may exist in numerous isomeric forms. The present invention is not limited to any single compound depicted or described but extends to include isomers thereof. For example, the compounds are not limited to a single structural isomer but include tautomers thereof. Tautomers are special structural isomers that are readily interconvertible through rapid equilibration. Likewise, the compounds are not limited to a single optical isomer but include enantiomers, diastereomers, and racemate mixtures thereof.

B. Bioactive Agents

The catechin multimer, particularly the substituted catechin multimer, may be administered alone or in combination with a suitable bioactive agent, preferably an agent directed against localized pathology. Examples of suitable bioactive agents contemplated by the present invention include but are not limited to anti-thrombotics, cholesterol lowering agents, anti-plaque agents, anti-cancer agents, chemotherapeutics, anti-inflammatory agents, antibiotics, antimicrobials, wound healing agents, and the like. Furthermore, in the context of the present invention, the bioactive agent may have more than one activity (i.e., fit into more than one category). For example, acetylsalycilic acid (i.e., aspirin) is considered to be both an anti-thrombotic agent and a general anti-inflammatory agent.

To facilitate formation of a complex with catechin, the bioactive agent should either be naturally nucleophilic and/or cationic or modified to be so. Although not wishing to be bound by theory, it is believed that nucleophilic bioactive agents react directly with catechin to create a catechin multimer; conversely, it is believed that cationic regions of bioactive reagents react and possibly replace one of the many carbon-linked protons or hydroxyl groups extending from the catechin multimer, so as to form a complex with the catechin multimer. A exemplary scheme is set forth below:

$$x\,[\text{cat}]+y\,[\text{BA}] \rightarrow [(cat)_{x'}-(\text{BA})_y-cat_{x''}]z$$

wherein cat refers to catechin, BA refers to bioactive agent (in its native form or as modified to be nucleophilic), and x, x', x", y, and z are integers including zero. The reaction may be repeated a number of times as described in Example 8. As a result, the BA moities are interspersed throughout the multimer, typically extending from the carbon linking units that connect the catechin monomers to each other. When administered in vivo, the catechin multimer targets the polar proteins residing in the vascular endothelium, cell walls and/or membranes. The bioactive agent is then released from the complex and allowed to provide localized benefit to the target site.

In one embodiment, the bioactive agent comprises limonene or a derivative thereof. Limonene [$C_{10}H_{16}$; CAS #5989-27-5] is monocyclic monoterpene occurring in nature as the main component of citrus peel oil, having a characteristic lemon-like fragrance. The molecular structure of limonene is shown below:

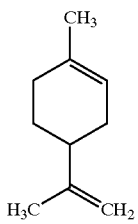

Chemical synonyms of limonene include: 4-isopropenyl-1-methylcyclohexene; acintene dipentene; cajeputene; cinene; dipanol; dipentene; kautschin; p-mentha-1,8-diene; dl-1,8 (9)-p-menthadiene; p-menthane; 1-p-mentha-1,8-diene; nesol; delta-1,8-terpodiene; methyl-4-isopropenyl-1-cyclohexene; and 1-methyl-4-(1-methylethenyl) cyclohexene. Limonene may comprise from about 1 wt. % to about 90 wt. %, preferably from about 5 wt. % to about 65 wt. %, more preferably from about 5 wt. % to about 55 wt. % of the total composition.

Limonene is commonly thought of as a solvent, having a KB value of 67. Recent findings suggest that limonene may inhibit the development of gastric cancers through increased apoptosis and decreased DNA synthesis (see Uedo et al., *Cancer Letters* (1999) 137:131–136). Limonene and perillyl alcohol together have been shown to induce apoptosis of human vascular smooth muscle cells (HVSMCs), an early cause of atherosclerosis (see Unlu S et al., *J of Cardiovasc Pharmacol* (February 2000) 35: 341). Preliminary ex-vitro trials of the present invention suggest that the introduction of limonene to human plasma can increase the rate of solubility of cholesterol by 24% over a one hour period; moreover, these same trials suggest limonene may aid in plasma metabolizing excess cholesterol at a minimum rate of 4% per hour (see Example 10). Likewise, limonene derivatives may enhance the activity of catechin multimers derivatives as demonstrated in a mean improvement in rabbits trials by over 20%.

In another embodiment, the bioactive agent comprises flavonoids or polyphenols, agents described in the literature as "cardiovascular protecting agents" (see U.S. Pat. No. 5,648,377; U.S. Pat. No. 4,707,360; Bohr D., *J. Pharmacol. Exp. Ther.* (1949) 97: 243; Haeger K. Zbl., *Phlebol.* (1967) 6:526; Allen S., *Practioner* (1970) 205:221; Gugler R., *Ces. Arch. Exp. Pathol. Pharm.* (1972) 247:45; Klurfeld, *Exp. Mol. Path.*(1981) 34:62; Lisunetz H., *Polyphenols,* (1990) 764; Frankel E., *Lancet* (1 993) 341:454; Kontek A., *Polyphenols* (1995) 94; Folts J., *Circul* (1995) 91: 1182; Yamakoshi et al. (1999) *Atherosclerosis* 142(1):139–49).

In a further embodiment, the bioactive agent comprises an anti-thrombotic agent. Exemplary anti-thrombotics include but are not limited to acetylsalicylic acid (e.g., aspirin), warfarin or coumadin.

In a further embodiment, the bioactive agent comprises a cholesterol-lowering agent, preferably comprising a carboxylic acid. Exemplary carboxylic acid cholesterol-lowering agents include statins, such as atorvastatin calcium (e.g., Lipitor®). Additional examples include Atromid-S™ (clofibrate), Choloxin™ (dextrothyroxine sodium), Lopid™ (gemfibrozil), Nicolar™ (niacin/nicotinic acid) and ciprolibrate.

In a further embodiment, the bioactive agent comprises an anti-cancer or chemotherapeutic agent. Exemplary anti-cancer agents include but are not limited to limonene, fluorinated cucurmin, calcium, folic acid, selenium, difluoromethylornithine, and resveratrol. Exemplary chemotherapeutics include but are not limited to fluorouracil (e.g., 5-fluorouracil), paclitaxel (sold under the tradename Taxol® by Bristol-Myers Squibb), cisplatin, cyclophosphamide, dacarbazine, dactinomycin, mechlorethamine, streptozocin, bleomycin, etoposide, methotrexate, chlorambucil, vincristine, vinblastine, mercaptopurine, and melphalan.

In a further embodiment, the bioactive agent comprises an anti-inflammatory agent. Exemplary suitable anti-inflammatory bioactive agents useful in the context of the present invention include but are not limited to steroids, such as corticosteroids like prednisone and non-steroidal anti-inflammatory drugs (or NSAIDS), such as indomethacin, aspirin and ibuprofen.

In a further embodiment, the bioactive agent comprises an antibiotic or antimicrobial agent. Exemplary antibiotics include but are not limited to beta-lactams such as penicillin and cephalosporin, aminoglycosides such as streptomycin and gentamycin, macrolides such as erythromycin, tetracyclines such as doxycycline, polypeptides such as polymyxin and bacitracin, and the like. Additional exemplary antimicrobials include, but are not limited to, salts of bismuth fluoride, chloride, sodium, and zinc. Preferred examples include, but are not limited to, sodium hydroxide, bismuth citrate, bismuth permanganate, bismuth difluoroketone, zinc citrate, zinc permanganate, and zinc difluoroketone.

In a further embodiment, the bioactive agent comprises a wound healing agent (i.e., an agent that promotes the healing of wounds and burns). Exemplary wound healing agents include but are not limited to growth factors and cytokines such as platelet derived growth factors (PDGFs), tumor necrosis factors (TNFs), fibroblast growth factors (FGFs), transforming growth factors (TGFs), interleukins, and keratinocyte growth factor-2 (or KGF-2 produced under the tradename Repifermin® by Human Genome Sciences) as well as nitric oxide releasing compounds, such as nitric oxide NONOates.

C. Pharmaceutical and Nutraceutical Formulations and Components Thereof

The therapeutic compositions of the present invention (e.g., the carrier-bioactive agent complex) may be pharmaceutically or nutraceutically formulated to include beneficial additives such as pharmaceutical carriers, diluents, buffers, adjuvants, excipients, surfactants and stabilizers. The amount of additive present may vary, ranging from about 0.1 wt. % to about 99 wt. %, preferably from about 5 wt. % to about 80 wt. %, more preferably from about 10 wt. % to about 70 wt. % of the total composition.

In a preferred embodiment, the therapeutic composition of the present invention comprises about 15 to about 85 wt. % substituted catechin (or a derivative thereof), from about 5 to about 65 wt. % limonene (or a derivative thereof), and, if present, about 20 wt. % to about 60 wt. % additional ingredient (e.g., an antioxidant stabilizer).

Although the therapeutic compositions of the present invention may be formulated "neat" (i.e., without excipients), an especially preferred embodiment comprises gallic acid (or a derivative thereof), limonene (or a derivative thereof), and lecithin, an excipient that acts as both an antioxidant stabilizer and a pH buffer. Lecithin and other phospholipids have been shown to particularly alleviate the gastrointestinal discomfort associated administration of certain bioactive agents, such as limonene.

As used herein, a composition or compound is "pharmaceutically acceptable" if it is suitable for use with humans and/or other animals without undue adverse side effects such as toxicity, irritation, and allergic response.

As used herein, the term "nutraceutical" refers to nutrition and food products, usually from natural sources, having some pharmaceutical benefits.

As used herein, the term "pharmaceutical carrier" refers to pharmaceutically acceptable solvents, suspending agents, liposomes and vehicles for delivering the therapeutic agent (s) to the animal, particularly a human. The carrier may be liquid or solid and varies with the selected administration route. When the carrier serves as a diluent (i.e., a substance that dilutes), it may be a solid, semi-solid, or liquid material acting as a vehicle, excipient, or medium for the active ingredient(s).

As used herein, the terms "buffer" and "buffering agent" refer to additives that adjust and maintain the pH value of a pharmaceutical solution or lyophilized preparation (i.e., the pH on reconstitution) within acceptable ranges. The buffering agents adjust the pH value of the pharmaceutical solution so that the stability of the active agent is maintained. Exemplary buffering agents include, but are not limited to, lecithin, phosphate buffer, Tris buffer and citrate buffer.

As used herein, an "adjuvant" is a substance that, when added to a pharmaceutical composition, either enhances or improves the therapeutic activity of one or more of the active agents contained therein or enhances the overall therapeutic effectiveness of the composition as a whole. A preferred adjuvant for use with the present therapeutic compositions is lecithin, a compound that cures the negative GI side effects of certain agents such as limonene as well as certain anti-cancer and/or chemotherapeutic agents.

As used herein, the term "pharmaceutical excipient" refers to any more or less inert, non-toxic substance added to a pharmaceutical composition in order to confer some benefit thereto, such as improved physical and/or chemical stability or improved handling characteristics (e.g., flowability and consistency). In other embodiments, the excipient merely serves as a bulking agent, reducing the concentration of the therapeutic agent in the pharmaceutical composition. Exemplary pharmaceutical excipients include, but are not limited to, proteins, peptides, amino acids, lipids, polymers, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which may be present singly or in combination.

As used herein, a "surfactant" is an excipient having surface activity/Exemplary surfactants include, but are not limited to, Tween 80, Tween 20, Pluronic F-68, polyethylene glycol, and the like.

Antioxidants, when exposed to air or water at room temperature, tend to be neutralized over time. In plasma, these neutralized "antioxidants" become "oxidants". For example, studies have shown that while fresh polyphenols, such as those found in grapes, can prevent atherosclerosis, those stored at room temperature for 18 months or more tend to enhance the causes of atherosclerosis. Thus, a preferred therapeutic composition will contain the proper stabilizing agent(s).

As used herein, a "stabilizer" is an excipient that improves the stability (e.g., the storage stability) of the pharmaceutical composition, helping to maintain the therapeutic activity of the active agent(s) disposed therein. Exemplary stabilizers include, but are not limited to, amino acids, such as glycine, and sugar alcohols, such as mannitol. The stabilizing agent preferably comprises from about 10 wt. % to about 60% wt. of the total therapeutic composition.

In a preferred embodiment, the stabilizer is an antioxidant. As used herein, the term "antioxidant" refers to synthetic or natural substances that prevent or delay the oxidative deterioration of a compound. Exemplary antioxidants include lecithin, gamma oryzanol; ubiquinone (ubidecarenone) and coenzyme Q; vitamins, such as vitamins A, C (ascorbic acid) and E and beta-carotene; natural components such as carnosol, carnosic acid and rosmanol found in rosemary and hawthorn extract, proanthocyanidins such as those found in grapeseed or pine bark extract, and green tea extract.

A preferred antioxidant for use with the therapeutic compositions of the present invention is lecithin, a compound that cures the negative GI side effects of limonene.

Homologs, analogs and derivatives of such antioxidants are also useful. For example, the principle active component of Vitamin E is tocopherol, particularly α-tocopherol; however, any Vitamin E or tocopherol derivative may be employed. Examples of useful Vitamin E derivatives include, but are not limited to, esters, for example, tocopherol acetate, tocopherol linoleate, tocopherol nicotinate, tocopherol sorbate, or tocopherol succinate; polyethylene glycol ethers of tocopherol, such as tocophereth-5, tocophereth-10, tocophereth-12, tocophereth-18 or tocophereth-50 and 6-hydroxychroman homologues, (such as are described in U.S. Pat. Nos. 4,003,919; 4,018,799; 4,026,907 and 3,903,317) particularly 6-hydroxy-2,5,7,8-tetramethylchroman-2-chroman-2-carboxylic acid, commercially available as Trolox-CT™ (Cort et al., *JAOCS* 52: 174, 1975) and Troloxyl-amino acids (Taylor et al., *JAOCS:* 622, 1981).

Examples of useful Vitamin C derivatives include, but are not limited to, ascorbyl esters of fatty acids, such as ascorbyl palmitate, ascorbyl dipalmitate, ascorbyl dimethylsilanol palmitate, and ascorbyl stearate; metal or metal phosphate salts, such as magnesium, sodium, or potassium ascorbyl phosphate, or magnesium, sodium or potassium ascorbate.

Ubiquinone is a naturally occurring hydrogen carrier in the respiratory chain(coenzyme Q); structurally, it is a 2,3-dimethoxy-5-methyl-1,4-benzoquinone with a multiprenyl side chain, the number of isoprene units varying depending upon the organism. Exemplary ubiquinone derivatives are described, for example, in WO 8803015.

D. Therapeutic Utilities

As discussed above, the therapeutic compositions of the present invention are useful as pharmaceuticals (e.g., drugs) or nutraceuticals (e.g., dietary supplements) for treating a variety of diseases and disorders, depending upon the bioactive agent to be delivered.

In one embodiment, the therapeutic compositions find utility in the treatment of stenotic vascular diseases and disorders, such as atherosclerosis and coronary artery disease, in patients in need thereof. While not wishing to be bound by theory, it is believed that the therapeutic compositions of the present invention aid in the prevention and encourage the removal of atherosclerotic plaques by keeping lipids and phospholipids in a more liquid state but also aids in unnecessary thrombocytes aggregation and leukocytes vascular adhesion. The varying concentrations of these compounds in the blood and their vasodilating tendencies aid in the natural removal of unwanted deposits on the endothelium layer by simple mechanical variation of the vascular walls via vasodilation and constriction. The changing of the threshold of thrombocyte aggregation also aids in preventing a sudden heart attack.

In another embodiment, the therapeutic compositions are useful in the treatment of diseases and disorders associated with localized pathology, such as cancer, inflammatory conditions, neurological conditions, infection, wounds, burns and the like. For example, the therapeutic compositions may find utility in the treatment of certain cancers, preventing or inhibiting tumor growth, aggregation, and progression.

In the context of the present invention, the term "animal" encompasses both humans and non-humans. The compositions and methods of the present invention are preferably directed to vertebrate animals, more preferably to mammals (including humans).

Likewise, in the context of the present invention, the term "patient" primarily refers to human subjects, although the formulations of the present invention are also useful in the treatment of animals other than humans.

The specific dosage amount of each active agent being administered to obtain therapeutic or inhibitory effects may be determined in a manner known in the art according to the particular circumstances surrounding the case, including, e.g., the specific agent being administered, the route of administration, the condition being treated, and the subject or host being treated. The total daily dose of a therapeutic composition, comprising of carrier (a catechin multimer or a derivative thereof), bioactive agent and optionally an additive (e.g., excipient or stabilizer), administered in single or multiple doses, may range from about 10 to 100,000 milligrams per day. The total daily dosage of the carrier-bioactive agent complex may range from about 1.5–8.5 to about 15,000–85,000 milligrams per day preferably from about 10 to 20,000 milligrams per day, more preferably from about 100 to 10,000 milligrams per day. The total daily dosage of the bioactive agent may range from about 0.5–6.5 to about 5000–80,000 milligrams per day, preferably from about 500 to 10,000 milligrams per day, more preferably from about 1000 to 10,000 milligrams per day.

The therapeutic compositions of the present invention may be administered by any of a variety of suitable routes, such as orally, parenterally, rectally, topically, transdermally, subcutaneously, intravenously, intramuscularly, and intranasally.

The agents are preferably formulated into compositions suitable for the desired routes before being administered. The therapeutic compositions may be prepared in any of a variety of forms suitable for the desired mode of administration. Exemplary forms include, but are not limited to, tablets, pills, capsules, powders, sprays, lotions, ointments, liquids, elixirs, suspensions, emulsions, solutions, sprays, aerosols, suppositories, and the like.

The particular dosage form should be selected to match the chosen route of administration. For example, if IV injection is the selected administration route, clearly the agents of the invention should be formulated into aqueous solutions, preferably in physiologically compatible buffers such as Hanks's solution, Ringer's solution, or physiological saline buffer.

The following examples illustrate aspects of the invention but in no way are intended to limit the scope of the present invention

EXAMPLES

The therapeutic pharmaceutical or nutritional compositions of the present invention may be formulated in a number of ways, using a number of art-accepted and routine techniques. Examples 1–3 describe methods of making substituted catechin multimers and catechin multimer complexes. Examples 4 and 5 describe studies that demonstrate and support the therapeutic utility of substituted catechin multimers alone in the treatment of thrombosis and atherosclerosis. Exemplary catechin-bioactive agent complexes and therapeutic uses thereof are described in Examples 6–10 below.

Example 1

Substituted catechin multimers have fewer adverse reactions than other more complex compounds of this invention and find utility in the treatment of many maladies, including but not limited to, atherosclerosis and mild anxiety. These compounds are made according to the following process:

Catechin was purchased from Sigma Chemical Company. 175 mg of catechin was dissolved in 100 $\mu$l water. The resulting slurry was exposed to 1.2 of 100% ammonia gas ($NH_3$) in a sealed vessel for 72 hours at room temperature. This treatment resulted in a marked color change in the catechin (from white to red-brown). At the end of the incubation period, the product was dissolved in water. Water and excess ammonia were then removed by lyophilization. The presence of an amidated catechin multimer was confirmed by HPLC. Over 20% of the catechin is converted to amidated catechin multimers.

These compounds are both potent agents for endothelium NO-cGMP signaling known to attenuate atherosclerosis and platelet aggregation inhibitors on endothelium and in plasma. This dual therapeutic benefit attenuates atherosclerosis and thrombosis. Certain of these amidated multimers are also mild calming agents.

Example 2

Catechin multimer—bioactive agent complexes of the present invention can be synthesized according to the following exemplary process or a process analogous thereto:

About 340 grams of a catechin, or a derivative thereof, is added to about 70 grams of a bioactive agent in about 800 ml of water. Varying amounts of additive compounds such as those described in the above Examples (i.e., ascorbic acid, lecithin, tannic acid, sodium hydroxide, bismuth citrate, bismuth permanganate, bismuth difluoroketone, zinc citrate, zinc permanganate, and zinc difluoroketone) may also be added. About 4 grams of ethoxylated alcohol may be added if needed. The mixture is then aerated with up to 8 grams of $O_2$ in an otherwise oxygen deprived vessel at 100° C. under reflux for up to 280 minutes. The temperature may be raised up to as much as 150° C. under reflux over 90 minutes, then cooled gradually. Fractional distillation and precipitation is started at $\Delta 25$ (see above) and a vacuum up to 10 psi is created to aid in chemical separation. Appropriate distillate columns are selected and used. The precipitated composition is then purified. The compositions may be particularly adjusted to correspond to a particular patient profile so as to minimize accumulation on and maximize the therapeutic potential of the composition.

Example 3

Phytochemicals in botanicals have been extracted by $CO_2$ critical phase extraction for over a decade. Ammonia, fluorine or other nucleophilic elements or compounds other than $CO_2$ may be used as the as the eluent. For example, prior to reaching the triple point, $NH_3$ gas can amidate catechin to increase yield of the desired therapeutic compositions (e.g., substituted catechin multimers or catechin multimers complexed with bioactive agents).

These therapeutic compositions can then be extracted from $NH_3$ below or above its' triple point. The therapeutic compositions described in all examples herein can be further purified via numerous art-accepted methods such as silica thin layer chromatography using hexane/ethyl acetate (8:2) as solvent system, dissolved in a halo-carbon solvent and t-butyl hydroperoxide (1:4). Likewise, the compositions can be conveniently separated by either column chromatography or thin layer chromatography or high pressure chromatography. Also, some compositions can be economically separated by $CO_2$ critical phase extraction.

Example 4

Human platelet aggregation trials, using PAF and thrombin as aggregating agents, were conducted with gallic acid, catechin and amidated catechin multimers (made according to the process of Example 1). The protocol was as follows:

Test compounds (50 $\mu$M gallic acid, 100 $\mu$M catechin and 3 $\mu$M amidated catechin multimer) were dissolved in water and 10 $\mu$l of sample was added to 1 ml aliquots of human platelets to give the final estimated vessel content concentration of 3 $\mu$M.[1] Next, human platelets at a concentration of $1\times10^{-7}$/ml were preincubated for ten minutes at 37° C. with either vehicle (contol) or with 3 $\mu$M of the amino-catechin multimer test compound. Then, either platelet activating factor ($5\times10^{-10}$ $\mu$M) or thrombin (0.05 mg/ml) were added and aggregation was monitored over the next 10 minutes in a PACKS-4 Platelet Aggregation Chromogenic Kinetic System (Helena Lab., Beaumont, Tex.).

[1] The molar concentration of total product was 10 $\mu$M. However, HPLC and mass spectrometry data (not shown) suggest that the actual molar concentration of the desired compound, amino-catechin multimer, was 3 $\mu$M. For molar calculations, the molecular weight of the amino-catechin was presumed to be 300 daltons.

Figure 1B:
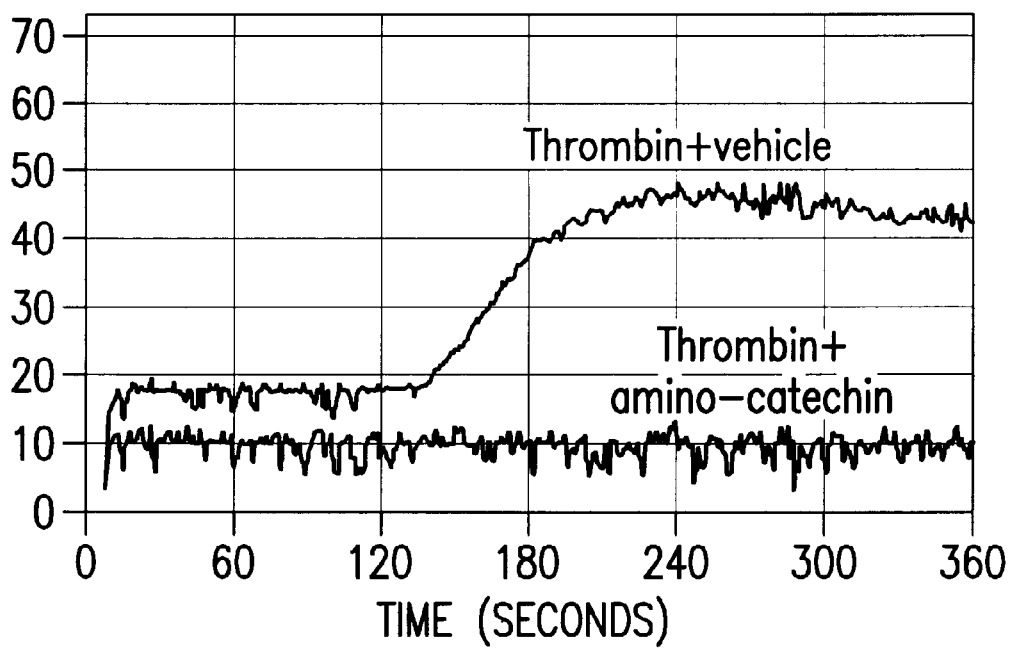
FIG. 1B depicts the results of human platelet aggregation trials using thrombin as the aggregating agent, comparing the effect of amidated catechin multimer to control. Time is shown on the X-axis and the percentage of platelets in aggregated state is shown on the Y-axis.

Results of platelet activating factor (PAF) assay, comparing amino-catechin multimer to control are shown in FIG. 1A attached hereto; likewise, results of thrombin assay, comparing amino-catechin multimer to control are shown in FIG. 1B attached hereto. Specifically, the amino-catechin multimer completely inhibited human platelet aggregation stimulated by both thrombin and platelet activating factor. In contrast, no inhibition of platelet aggregation caused by thrombin and platelet activating factor resulted from treatment with either 100 μM catechin or 50 μM gallic acid.

Example 5

Experiments were conducted using the amidated catechin multimers of Example 1 to determine their affect on the endothelium dependent relaxation of rat aortic rings. The protocol was as follows:

Male Sprague-Dawley rats (200–250 g) were euthanized with an overdose of sodium pentobarbital (100 mg/kg, i.p.) and bled. The thoracic aorta was excised and cleaned and rings 3–4 mm in length were cut, taking care not to disturb the endothelium The rings were suspended in tissue baths containing a physiologic salt solution. The solution was bubbled continuously with $O_2/CO_2$ (95%/5%), and maintained at 37° C. Contraction activity was recorded on a Grass polygraph. After equilibration for at least 1 h under 1.5 g of tension, tissues were contracted submaximally (approximately 80% of Emax) with 1 μM phenylephrine. Then, 3 μM acetylcholine, a known EDR-active compound, was added to the bath to test for intactness of the endothelium. This concentration of acetylcholine is sufficient to produce maximum endothelium dependent relaxation in intact rings.

The mean (±SEM) $EC_{50}$ value for phenylephrine to acetyline choline was 0.14±0.02 μM whereas the $EC_{50}$ for EDR to acetylcholine was 0.12±0.06 μM. The $EC_{50}$ value indicates the sensitivity of aortic rings to the contractile effects of the test compound.

Rings were washed with physiological salt solution three times over the next 45 min. prior to the subsequent testing. Beginning with a concentration determined in preliminary experiments to be below the threshold for relaxation, and increased until a relaxation of approximately 15% was achieved (relative to the relaxation induced by 3 μM acetycholine). The amidated catechin multimers described above showed an $Ec_{50}$ of between one and two which is very potent on the EC scale. It is multiple factors greater than the $Ec_{50}$ value of catechin and gallic acid per se. This elevated $Ec_{50}$ value is indicative of the promotion of endothelium NO-cGMP signaling, which correlates to an attenuation of atherosclerosis.

Example 6

A catechin multimer, such as the substituted catechin multimer described in Example 1, may be mixed with a bioactive monoterpene, such as limonene, in a molar ratio ranging form 1:3 to 1:10. The monoterpene reacts with the catechin multimer to yield a complex wherein the monoterpene is embedded in the multimeric structure of the catechin multimer. Catechin multimers having a strong affinity for endothelium and cellular proteins deliver monoterpenes to the vascular endothelium to solubilize excessive lipids that accumulate thereon. Thus, unlike most "statins", which operate by removing cholesterol from the liver, and other oral cholesterol lowering agents which operate by removing cholesterol from the blood, the monoterpene-catechin multimeric complex allows for localized therapy, operating at the site of pathology (i.e., the atherosclerotic plaque).

Monoterpenes may also be useful in cancer therapy. The inner mitochondrial membrane potential is an important aspect of mitochondrial cytochrome c release necessary for proper apoptosis, a process that is disturbed in malignant conditions. Though not wishing to be bound by theory, monoterpenes proper may mediate mitochondrial membrane potential, which then stimulates the release of cytochrome c and apoptosis in cancer cells.

Example 7

A catechin multimer, such as the amidated catechin multimer described in Example 1, may be mixed with a bioactive anti-hyperlipoproteinenic compound, such as carboxylic acid bioactive agent (e.g., ciprolibrate, statins, etc.). The pendant nucleophilic units (e.g., carboxylic acids) in some instances react with the pendant hydroxyl groups of catechin to yield a carboxylic acid-catechin complex. Catechin multimers have a strong affinity for endothelium proteins. Thus, carboxylic acids, common components in statins and other anti-hyperlipoproteinenic agents, are delivered via the catechin multimer to the vascular endothelium. There, they inhibit adhesion of platelets and macrophages while reducing lipid vascular lesions. These bioactive catechin complexes allow for localized therapy, operating at the site of pathology (i.e., the arterial endothelium).

Example 8

Potent delivery of chemotherapy agents to the proper local is a major components of cancer therapy. 5-Fluorouracil, taxol, fluorinated cucurmin or resveratrol or other chemotherapy agents can be attached to catechin multimers according to the process described in Example 2 above. Alternatively, the catechin—agent complex can be synthesized according to the following exemplary process or a process analogous thereto:

Catechin (or a derivative thereof) is mixed with a bioactive agent, such as fluorouracil, in water and slurried in $NH_3$ as described in Example 1. Glucose is optionally added to the mixture. Mass spectrometry data (not shown) suggests that ammonia is not incorporated into the complex. Thus, although not wishing to be bound by theory, it appears that ammonia acts as a catalyst, driving the formation of the complex between catechin and fluorouracil. The resulting product is dried and can be used to prevent metastasis of cancer cells.

After aggressive chemotherapy, therapeutic compounds containing fluorouracil in the core of a catechin multimer are given in low dosages to promote apoptosis of small metastasis cancer cell groups. Generally, cancer cells consume much larger amounts of sugar than non-cancerous cells. Accordingly, the anti-cancer activity of these compounds may be further augmented by adding additional catechin to the dry fluorouracil-catechin complex and repeating the initial ammonia and water reaction, so as to form larger multimers with fluorouracil deeply embedded therein and to create outer portions made of rutin exterior. These catechin based multimers tend to coat the vascular linings because of their high affinity to the vascular proteins. Metastasis cancer cells adjoining the vascular linings tend to absorb these sugar-coated compounds at a higher rate than normal cells. Hence, since catechin have a strong affinity for the vascular endothelium and cellular proteins, the use of the catechin multimer carriers can dramatically increase the fluorouracil concentration in cancer versus non cancerous cells. Once inside the cancer cell, fluorouracil masquerades as a legitimate nucleic acid building block thereby stopping the production of essential nucleic acid polymers. The cancer cells die. Accordingly, survival rates and patient comfort is increased while adverse reactions arising from the targeting of normal cells as are decreased.

Example 9

A catechin multimer—selenium complex may be prepared according to a process analogous to that described in Example 8 above, wherein fluorouracil is exchanged for a selenium compound such as a selenosulfite, selenide, selanozofurin, or selenous acid. The resulting complex finds therapeutic utility in the treatment of cancer.

Example 10

Some apolipoproteins, for example A-1, E2, E3, are beneficial in preventing plaque deposition, which is a critical mechanism in the development and progression of both atherosclerosis and Alzheimer's disease. Recent developments in the art have synthesized shorter peptides/proteins representing some bioactive segments of these proteins. These shorter bioactive peptides/proteins can be complexed with catechin multimers, such as a substituted catechin multimer produced according to the process of Example 1, in a manner analogous to the processes discussed above. The pendant nucleophilic units of the bioactive peptides react with the pendant hydroxyl groups of catechin to yield a complex wherein the bioactive peptide is embedded in the multimeric structure of the catechin multimer. Catechin multimers, particularly substituted catechin multimers, have a strong affinity for endothelium and cellular proteins. The embedded bioactive peptide is delivered via the catechin multimer to the vascular endothelium.

The disclosure of each publication, patent or patent application mentioned in this specification is specifically incorporated by reference herein in its entirety.

The invention has been illustrated by reference to specific examples and preferred embodiments. It should be understood that the invention is intended not to be limited by the foregoing description, but to be defined by the appended claims and their equivalents.

What is claimed:

1. A method for treating stenotic cardiac and vascular disorders in animals comprising administering to a subject in need thereof an effective amount of a therapeutic composition comprising of a substituted catechin multimer or a derivative of a substituted catechin multimer.

2. The method of claim 1, wherein said substituted catechin multimer is substituted with a nucleophilic substituent selected from the group consisting of halo, guano, amino, amido, nitro, cyano, carbonyl, carboxy, sulfo, sulfoxy, and aceto groups.

3. The method of claim 1, wherein said substituted catechin multimer comprises an amidated catechin multimer.

4. The method of claim 1, wherein said substituted catechin multimer comprises a fluorinated catechin multimer.

5. The method according to claim 1, wherein said composition further comprises an effective amount of cholesterol lowering agent.

6. A method according to claim 1, wherein said composition further comprises an effective amount of limonene or a derivative thereof.

7. The method according to claim 6, wherein said limonene derivatives are selected from the group consisting of perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

8. The method according to claim 1, wherein said composition is pharmaceutically formulated with an effective amount of an antioxidant stabilizing agent.

9. The method according to claim 1, wherein said composition is formulated with an antimicrobial agent selected from the group consisting of sodium hydroxide, bismuth citrate, bismuth permanganate, bismuth difluoroketone, zinc citrate, zinc permanganate, and zinc difluoroketone.

10. A therapeutic composition comprising a bioactive agent complexed with a carrier agent, wherein said bioactive agent is cationic or nucleophilic and said carrier agent comprises a catechin multimer.

11. The composition of claim 10, wherein said catechin multimer comprises a substituted catechin multimer.

12. The composition of claim 11, wherein said substituted catechin multimer is substituted with a nucleophilic substituent selected from the group consisting of halo, guano, amino, amido, nitro, cyano, carbonyl, carboxy, sulfo, sulfoxy, and aceto groups.

13. The composition of claim 11, wherein said substituted catechin multimer comprises an amidated catechin multimer.

14. The composition of claim 11, wherein said substituted catechin multimer comprises a fluorinated catechin multimer.

15. The composition of claim 10, wherein said bioactive agent is naturally nucleophilic.

16. The composition of claim 10, wherein said bioactive agent is modified to be nucleophilic.

17. The composition of claim 10, wherein said bioactive agent is selected from the group consisting of anti-thrombotics, cholesterol lowering agents, anti-plaque agents, anti-cancer agents, chemotherapeutics, anti-inflammatory agents, antibiotics, antimicrobials, and wound healing agents.

18. A method for targeting the delivery of a bioactive agent to select cellular or tissue targets comprising administering to a patient in need thereof the therapeutic composition of claim 10.

19. A method for treating a disease or disorder associated with localized pathology comprising administering to a patient in need thereof the therapeutic composition of claim 10.

20. The method of claim 19, wherein said disease or disorder is selected from the group consisting of cardiac and vascular stenoses, cancer, inflammatory conditions, neurological conditions, infections, wounds, and burns.

21. A method for treating stenotic cardiac and vascular disorders in animals comprising administering to a subject in need thereof an effective amount of a therapeutic composition comprising of a substituted catechin multimer or a derivative thereof, wherein said substituted catechin multimer is substituted with a nucleophilic substituent selected from the group consisting of guano, amino, amido, nitro, cyano, carbonyl, carboxy, sulfo, sulfoxy, and aceto groups.

\* \* \* \* \*